United States Patent
Claremon et al.

[11] Patent Number: 5,691,331
[45] Date of Patent: Nov. 25, 1997

[54] N-(2,4-DIOXO-2,3,4,5-TETRAHYDRO-1H-1,5-BENZODIAZEPIN-3YL) -3- AMIDES

[75] Inventors: David A. Claremon, Maple Glen; Roger M. Freidinger, Lansdale; Nigel Liverton, Harleysville; Harold G. Selnick, Ambler; Garry R. Smith, East Norriton, all of Pa.

[73] Assignee: Merck & Co., Inc., Rahway, N.J.

[21] Appl. No.: 474,801

[22] Filed: Jun. 7, 1995

[51] Int. Cl.$^6$ .................... A61K 31/55; C07D 243/12
[52] U.S. Cl. ............................. 514/221; 540/506
[58] Field of Search .................. 514/221; 540/506

[56] References Cited

U.S. PATENT DOCUMENTS

| | | | |
|---|---|---|---|
| 4,470,988 | 9/1984 | Watthey | 424/263 |
| 4,473,575 | 9/1984 | Watthey | 424/263 |
| 4,503,060 | 3/1985 | Walther et al. | 514/214 |
| 4,507,313 | 3/1985 | Braestrap et al. | 514/220 |
| 4,537,885 | 8/1985 | Watthey | 514/183 |
| 4,600,534 | 7/1986 | Bach et al. | 260/239 |
| 4,692,522 | 9/1987 | Parsons et al. | 540/523 |
| 4,775,671 | 10/1988 | Hunkeler et al. | 514/220 |
| 4,820,834 | 4/1989 | Evans et al. | 540/504 |
| 4,847,248 | 7/1989 | Freidinger et al. | 514/214 |
| 4,992,437 | 2/1991 | Naka et al. | 514/220 |
| 5,004,741 | 4/1991 | Evans et al. | 514/221 |
| 5,055,464 | 10/1991 | Murakami et al. | 514/211 |
| 5,166,151 | 11/1992 | Freidinger et al. | 514/215 |
| 5,206,234 | 4/1993 | Bock et al. | 514/213 |
| 5,220,018 | 6/1993 | Bock et al. | 540/509 |
| 5,302,591 | 4/1994 | Fletcher et al. | 514/221 |
| 5,324,726 | 6/1994 | Bock et al. | 514/221 |
| 5,338,861 | 8/1994 | Botta et al. | 548/552 |
| 5,360,802 | 11/1994 | Chambers et al. | 514/221 |
| 5,410,049 | 4/1995 | Chambers | 540/504 |
| 5,426,185 | 6/1995 | Baldwin et al. | 540/509 |
| 5,428,157 | 6/1995 | Baldwin et al. | 540/509 |
| 5,438,055 | 8/1995 | Baldwin et al. | 514/221 |
| 5,439,905 | 8/1995 | Naka et al. | 514/220 |
| 5,439,906 | 8/1995 | Bock et al. | 514/220 |
| 5,504,077 | 4/1996 | Collins et al. | 514/211 |

FOREIGN PATENT DOCUMENTS

| | | |
|---|---|---|
| 1 190 708 | 7/1985 | Canada. |
| 0 107 095 A1 | 5/1984 | European Pat. Off.. |
| 0 514 133 A1 | 11/1992 | European Pat. Off.. |
| 0 538 945 A1 | 4/1993 | European Pat. Off.. |
| 0 566 175 A2 | 10/1993 | European Pat. Off.. |
| WO93/02078 | 2/1993 | WIPO. |
| WO 93/08176 | 4/1993 | WIPO. |
| WO/9307131 | 4/1993 | WIPO. |
| WO 93/15068 | 8/1993 | WIPO. |
| WO 93/17011 | 9/1993 | WIPO. |
| WO 93/19063 | 9/1993 | WIPO. |
| WO 94/05673 | 3/1994 | WIPO. |

OTHER PUBLICATIONS

J. Gen. Physiol., vol. 96, pp. 195–215 (Jul. 1990), by M. C. Sanguinetti, et al.

J. Cardiovasc. Pharmacol., vol. 20, (Suppl. 2) pp. S17–S22 (1992), by L. M. Hondeghem.

Chemical Abstract No. 114:62127c, vol. 114, issued 1991, Gasc, et al.

Chemical Abstract No. 120:134541g, vol. 120, issued 1994, Finch, et al.

Chemical Abstract No. 120:164241b, vol. 120, issued 1994, Trist, et al.

*Primary Examiner*—John M. Ford
*Attorney, Agent, or Firm*—Elliott Korsen; Francis P. Bigley; Mark R. Daniel

[57] ABSTRACT

This invention is concerned with novel compounds represented by structural formula I

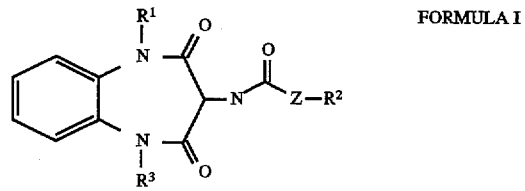

FORMULA I which are useful in the treatment of arrhythmia.

12 Claims, No Drawings

N-(2,4-DIOXO-2,3,4,5-TETRAHYDRO-1H-1,5-BENZODIAZEPIN-3YL) -3- AMIDES

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, agents which exhibit both satisfactory effects and high safety profiles have not been marketed. For example, antiarrythmic agents of Class I, according to the classification of Vaughan-Williams, which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drags which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

SUMMARY OF THE INVENTION

This invention is concerned with novel compounds represented by structural formula I

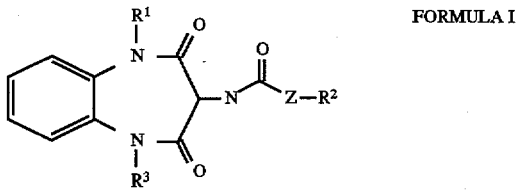

FORMULA I where $R^1$ and $R^3$ are independently $C_{1-6}$ alkyl, either straight or branched chain; substituted $C_{1-6}$ alkyl, either straignt or branched chain wherein the substitutents are selected from F, $C_{3-8}$ cycloalkane, —OH, —$CF_3$, and Z is 1) $C_{1-6}$ alkyl, either straight or branched chain, 2) substituted $C_{1-6}$ alkyl, either straignt or branched chain, wherein the substitutents are selected from F, OH, $NO_2$, 2) $C_{2-4}$ alkenylene, either straight or branched chain, 3) —$(CH_2)_m$—W—$(CH_2)_n$— wherein m and n are independently 0, 1, 2, 3 or 4 and W is —O—, —S— or —NH, 4) C3-6 cycloalkane, 5) $C_{3-6}$ cycloalkylene, or 6) single bond;

$R^2$ is 1) phenyl, either unsubstituted or substituted with one or two subsfituents selected from
 a) —$NO_2$, OH,
 b) 'Cl, Br, F, or I,
 c) —$CF_3$,
 d) —$C_{1-3}$ alkyl,
 e) —$C_{1-3}$ alkoxy,
 f) —CN,
 g) -methylenedioxy, 2) $C_{5-7}$ cycloalkyl, either unsubstituted or substituted with one or two substitutents selected from
 a) —$NO_2$,
 b) —F,
 c) —$CF_3$,
 d) —$C_{1-3}$ alkyl,
 e) —$C_{1-3}$ alkoxy,
 f) —CN,
 g) -methylenedioxy, or pharmaceutically acceptable salts, hydrates and crystal forms thereof, which are useful as antiarrhythmic agents.

The compounds of the present invention may have asymmetric centers and occur as racemates, mixtures of enantiomers, individual diastereomers, or as individual enantiomers with all isomeric forms being included in the present invention. The invention is also concerned with pharmaceutical formulations comprising one of the novel compounds as an active ingredient.

The invention is also concerned with a method of treating arrhythmia by the administration of one or a combination of the novel compounds or formulation thereof to a patient in need of such treatment.

DETAILED DESCRIPTION OF THE INVENTION

The novel compounds of this invention have structural formulae

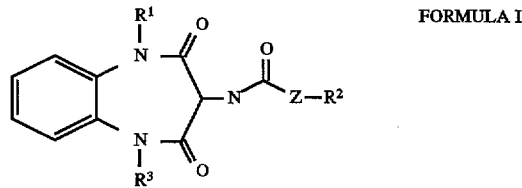

FORMULA I where $R^1$ and $R^3$ are independently $C_{1-6}$ alkyl,either straight or branched chain; substituted $C_{1-6}$alkyl, either straight or branched chain wherein the substitutents are selected from F, $C_{3-8}$ cycloalkane, —OH, —$CF_3$, and Z is 1) $C_{1-6}$ alkyl, either straight or branched chain, 2) substituted $C_{1-6}$ alkyl, either straignt or branched chain, wherein the substitutents are selected from F, OH, $NO_2$, 2) $C_{2-4}$ alkenylene, either straight or branched chain, 3) —$(CH_2)_m$—W—$(CH_2)$n— wherein m and n are independently 0, 1, 2, 3 or 4 and W is —O—, —S— or —NH, 4) $C_{3-6}$ cycloalkane, 5) $C_{3-6}$ cycloalkylene, or 6) single bond;

$R^2$ is 1) phenyl, either unsubstituted or substituted with one or two substituents selected from
   a) —$NO_2$, —OH,
   b) —Cl, Br, F, or I,
   c) —$CF_3$,
   d) —$C_{1-3}$ alkyl,
   e) —$C_{1-3}$ alkoxy,
   f) —CN,
   g) -methylenedioxy, 2) $C_{5-7}$ cycloalkyl, either unsubstituted or substituted with one or two substitutents selected from
   a) —$NO_2$,
   b) —F,
   c) —$CF_3$,
   d) —$C_{1-3}$ alkyl,
   e) —$C_{1-3}$ alkoxy,
   f) —CN,
   g) -methylenedioxy, or pharmaceutically acceptable salts, hydrates and crystal forms thereof, which are useful as antiarrhythmic agents.

The compounds of the present invention may have asymmetric centers and occur as racemates, mixtures of enantiomers, individual diastereomers, or as individual enantiomers with all isomeric forms being included in the present invention. The invention is also concerned with pharmaceutical formulations comprising one of the novel compounds as an active ingredient.

The invention is also concerned with a method of treating arrhythmia by the administration of one or a combination of the novel compounds or formulation thereof to a patient in need of such treatment.. These compounds include pharmaceutically acceptable crystal forms and hydrates of the compounds of Formula I, which are antiarrhythmic agents.

One embodiment of the novel compounds of this invention which is synthesized using the process of Scheme I and is shown in Example 1 is N-(2,4-Dioxo- 1,5-bis-(2-propyl)-2,3,4,5-tetrahydro-1H-1,5-benzodiazepin-3-yl)-3-cyclohexyl propionamide

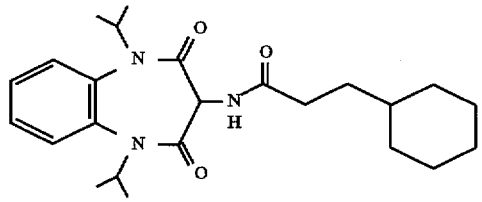

An other embodiment of the novel compounds of this invention is N-(2,4-Dioxo-1-5-bis(2-propyl)-2,3,4,5-tetrahydro-1H-1,5-benzodiazepin-3-yl)-3-(2,4-dichlorophenyl) propionamide.

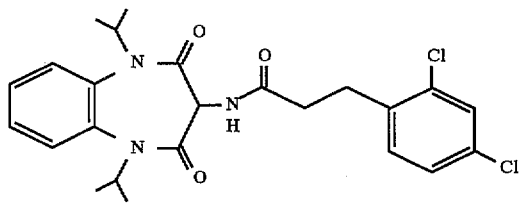

The synthesis of this compound is shown diagramatically in Scheme I and is fully explained in Example 2.

An other embodiment of the novel compounds of this invention is N-(2,4-Dioxo-1-5-bis(2-propyl)-2,3,4,5-tetrahydro-1H-1,5-benzodiazepin-3-yl)-2-(3,5-dichlorophenyl) acetamide.

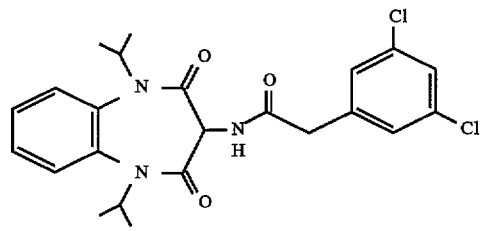

The synthesis of this compound is shown diagramatically in Scheme I and is fully explained in Example 3.

An other example of the novel compounds of this invention is N-(2,4-Dioxo-1-5-bis(2-propyl)-2,3,4,5-tetrahydro-1H-1,5-benzodiazepin-3-yl)-2-(2,4-dichlorophenyl) acetamide.

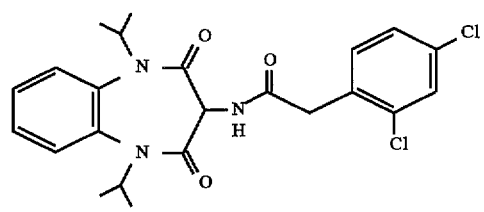

The synthesis of this compund is shown diagamatically in Scheme I and is fully explained in Example 4.

Still an other embodiment of the novel compounds of this invention is N-(2,4-Dioxo-1-5-bis(2-propyl)-2,3,4,5-tetrahydro-1H-1,5-benzodiazepin-3-yl)-3,4-dichlorobenzamide.

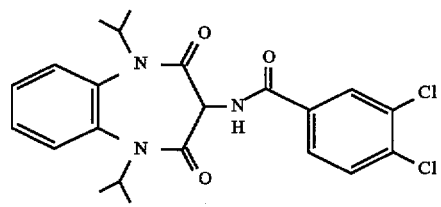

The synthesis of this compound is shown diagramatically in Scheme I and is fully explained in Example 5.

Yet an other example of the novel compunds of this invention is N-(2,4-Dioxo-1-(2-propyl)-5-(2,2,2-trifluoroethyl)-2,3,4,5-tetrahydro-1H-1,5-benzodiazepin-3-yl)-2-(3,5-dichlorophenyl) acetamide

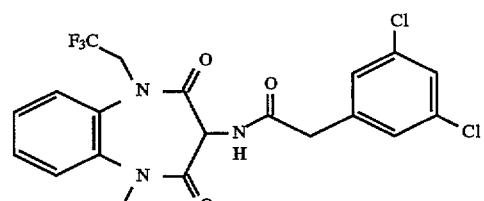

The synthesis of this compund is shown diagramatically in Scheme II and is fully explained in Example 6.

Still an other example of the novel compounds of this invention is N-(2,4-Dioxo-1-(2-propyl)-5-(2,2,2-trifluoroethyl)-2,3,4,5-tetrahydro-1H-1,5-benzodiazepin-3-yl)-2-(2,4-dichlorophenyl) acetamide

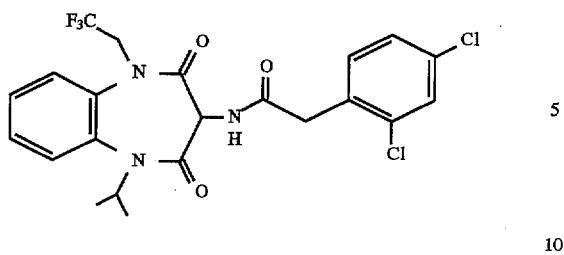
The synthesis of this compound is shown diagamatically in Scheme II and is fully explained in Example 7.
The novel processes for preparing the compounds of this invention are schematically exemplified below in schemes I and II. These steps are well known in the art and/or described in the Examples that follow.
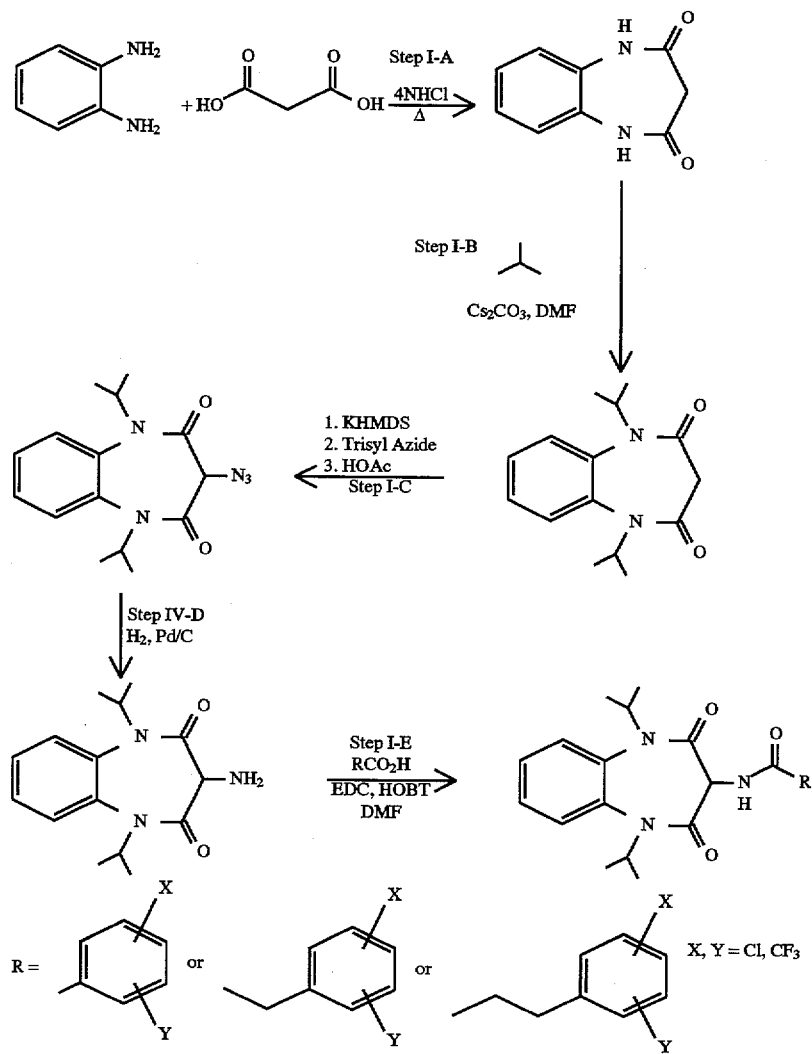

Scheme II

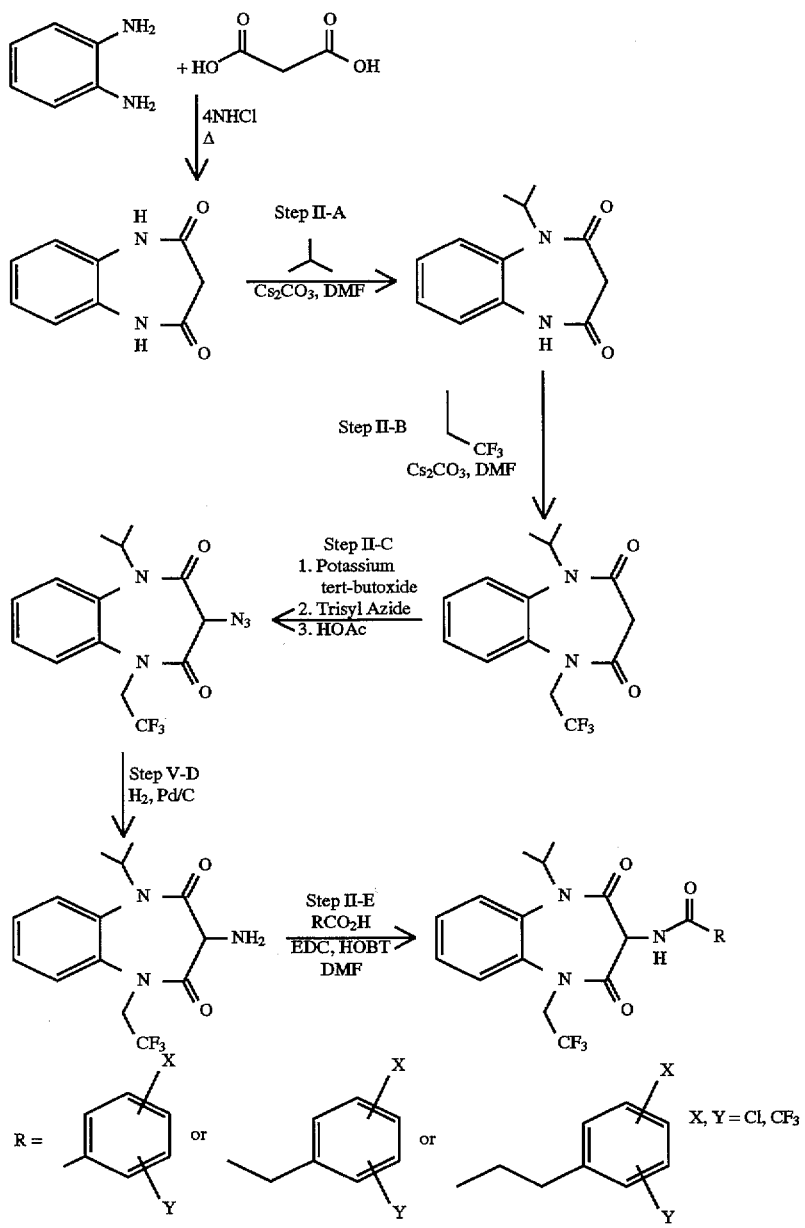

The novel compounds of the present invention, have the pharmacological properties required for antiarrhythmic agents of Class III, namely the prolongation of the myocardial action potential in vitro, without a significant depression of the Vmax, and the prolongation of QTc-interval in anesthetized dogs.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 5.0 mg per kg of body weight per day in a single dose or in 2 to 4 divided doses.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, emulsions, syrups, wafers, chewing gum, or the like prepared by art recognized procedures. The amount of active compound in such therapeutically useful compositions or preparations is such that a suitable dosage will be obtained.

These compounds can be administered as the sole active ingredient or in combination with other antiarrhythmic agents or other cardiovascular agents, such as Class I, Class II or Class IV antiarrhythmic agents, vasodilators, angiotensin converting enzyme inhibitors, angiotensin II antagonists, diuretics or digitalis.

These compounds can be administered as a method of treating arrhythmia and impaired cardiac pump functions in conjunction with defibrillators, including implantable defibrillators. These compounds reduce the frequency of defibrillator firing.

By Class I antiarrhythmic agents is meant those agents which provide for sodium channel blockade, including those compounds which exert a membrane stabilizing effect. Exemplary of this class of compounds are quinidine, procainamide, disopyramide, lidocane, tocainide, flecainide and propafenone. By Class II antiarrhythmic compounds is meant those agents which block sympathetic activity. Exemplary of this class of compounds are propranolol and acebutolol. By Class III antiarrhythmic agents is meant those compounds which prolong the effective refractory period without altering the resting membrane potential or rate of depolarization. In addition to the novel compounds of this invention, compounds such as amiodarone, bretylium and sotalol are considered to be in this class. Class IV antiarrhythmic agents are effective in calcium channel blockade. Exemplary of this class of compounds are diltiazem and verapamil. Further definition of these classes can be found in Pharma Projects, section C1B, May 1993, which is hereby incorporated by reference.

Exemplary of vasodilators are compounds such as papaverine and isosorbide dinitrat. Examples of angiotensin converting enzyme inhibitors include enalapril, lisinopril and captopril. Examples of diuretics include hydrochlorothiazide and acetazolamide. The pharmaceutical agents listed herein are examples and do not represent a complete listing of the many compounds in these classes which are contemplated by this invention.

The activity of the compounds described herein as antiarrhythmic agents is measured by their ability to block the IKs and IKr currents as determined by the following test protocol.

Outward potassium currents are measured in single guinea pig ventricular myocytes using a whole-cell voltage clamp technique described in detail elsewhere (Sanguinetti and Jurkiewicz, 1990, Two components of cardiac delayed rectifier K$^+$ current: differential sensitivity to block by Class III antiarrhythmic agents. J. Gen Physiol. 96: 195–215). Myocytes are isolated by enzymatic (collagenase and protease) digestion of Langandorf perfused hearts. Single cells are then voltage clamped using 1 mm square-bore pipettes filled with 0.5M Kgluconate, 25 mM KCl, 5 mM K(2)ATP. Cells are bathed in a solution containing, in mN: 132 NaCl, 4KCl, 1.2 MgCl[2], 10 HEPES, 10, glucose: pH 7.2, temp. 35° C.

Each cell is maintained at a holding potential of −50 mV. Test depolarizations are applied as voltage ramps from −85 to −50 mV (0.5 s) and as steps to −10 mV (0.5 s) and +50 mV (1.0 s). IKI is measured as peak outward current during the voltage ramp. IKr is measured as tail currents upon repolarization from −10 mV to −50 mV. IKs is measured as time-dependent current during the pulse to +50 mV. Currents are measured during control, then after exposure to drug at two different concentrations.

Employing this test the compounds described herein have an IC$_{50}$ of less than 1,000 nM as IKs blockers. The comounds of this invention are at least 10 times more potent in the blockade of IKs than the blockade of IKr.

EXAMPLES

In the following examples, reference is made to the steps outlined of the schemes found in the Detailed Description of the Invention. For example, "Step I-A" refers to Step A of Scheme I.

Example 1

N-(2,4-Dioxo-1,5-bis-(2-propyl)-2,3,4,5-tetrahydro-1H-1,5-benzodiazepin-3-yl)-3-cyclohexyl propionamide

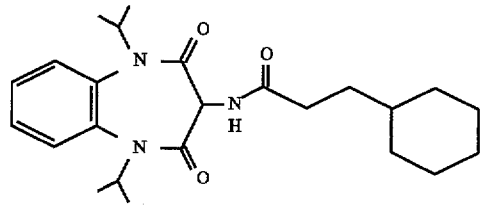

Step I-A: 1,5-benzodiazepine-2,4-dione

A suspension of o-phenylenediamine (10.8g, 0.1 mole) and malonic acid (5.2g, 0.05 mole) in 4N HCl (50 mL) was heated to 80° C. for 3 hours. The reaction was cooled to room temperature and the solid collected by filtration to give 8 g.

$^1$H NMR (300 MHz, d6-DMSO) d 10.40 (s, 1H), 7.20–7.08 (m, 4H), 3.08 (s, 2H),

Step I-B: 1,5-(Bis-2-propyl)-1,5-benzodiazepine-2,4-dione A solution of 1,5-benzodiazepin-2,4-dione (10 g, 0.057 mole) in N,N-dimethylformamide (80 mL) at room temperature was treated with cesium carbonate (40.7 g, 0.125 mole) and 2-iodopropane (21.28 g, 12.5 mL, 0.12 mole), and the reaction was stirred at room temperature for five hours. The reaction was poured into a solution of saturated sodium hydrogen carbonate (600 mL) and extracted with ethyl acetate (3×300 mL). The organic layers were combined, dried over anhydrous magnesium sulfate, filtered, and concentrated in vacuo. The residue was chromatographed on silica gel eluting with 1:1 ethyl acetate:hexane to give 7.2 g of product (49%). $^1$H NMR (300 MHz, CDCl$_3$) d 7.43–7.35 (m, 2H), 7.30–7.23 (m, 2H), 4.55 (sep, J=7.0 Hz, 2H), 3.26.(d, J=12.2 Hz, 1H), 3.18 (d, J=12.2 Hz, 1H), 1.53 (d, J=6.9 Hz, 6H), 1.23 (d, J=7.0 Hz, 6H).

Step I-C: 3-Azido-1,5-Bis-(2-propyl)-1,5-benzodiazepine-2,4-dione

To a stirring solution of 1,5-bis-(2-propyl)-1,5-benzodiazepin-2,4-dione (500 mg, 1.92 mmole) in tetrahydrofuran (25 mL), which was cooled to −78° C. in a dry ice/acetone bath, was added dropwise potassium bis (trimethylsilyl) amide (0.5M in toluene, 4.6 mL, 2.3 mmole). After ten minutes, 2,4,6-triisopropylbenzenesulfonyl azide (708 mg, 2.0 mmole) in tetrahydrofuran (5 mL) was added dropwise. After ten minutes, acetic acid (0.44 mL, 7.7 mmole) in tetrahydrofuran (5 mL) was added in one portion and the reaction was warmed to room temperature over three hours. The reaction was poured into a solution of saturated sodium hydrogen carbonate (200 mL) and extracted with ethyl acetate (3×100 mL). The organic layers were combined, dried over anhydrous magnesium sulfate, filtered, and concentrated in vacuo. The residue was chromatographed on silica gel eluting with 1:3 ethyl acetate:hexane to give 315 mg of an isomer that is identified as the axial azide, and 120 mg of a lower rf isomer identified as the equatorial conformer. NMR dam for the major isomer is:

$^1$H NMR (300 MHz, CDCl$_3$) d 7.40–7.33 (m, 2H), 7.33–7.28 (m, 2H), 4.90 (s, 1H), 4.50 (sep, J=7.0 Hz, 2H), 1.52 (d, J=6.9 Hz, 6H), 1.30 (d, J=7.0 Hz, 6H).

Step I-D: 3-Amino-1,5- Bis-(2-propyl)-1,5-benzodiazepine-2,4-dione

To a stirring suspension of 10% Pd/C (90 mg) in ethanol (10 mL) was added a solution of 3-azido-1,5-bis-(2-propyl)

-1,5-benzodiazepin-2,4-dione (200 mg, 0.70 mmole) in ethanol (10 mL). The mixture was hydrogenated at 50 psi H₂ on a Parr apparatus for 4 hours. The catalyst was filmred off and the ethanol evaporated at reduced pressure to give the product amine (200 mg).

¹H NMR (300 MHz, CDCl₃) d 7.45–7.38 (m, 2H), 7.35–7.28 (m, 2H), 4.53 (sep, J=7.0 Hz, 2H), 4.40 (s, 1H), 1.53 (d, J=6.9 Hz, 6H), 1.26 (d, J=7.0 Hz, 6H).

Step I-E: N-(2,4-Dioxo-1,5-bis-(2-propyl)-2,3,4,5-tetra-hydro1H-1,5-benzodiazepin-3-yl)-3-cyclohexyl propionarnide To a stirring solution of 3-amino-1,5-bis-(2-propyl)-1,5-benzodiazepin-2,4-dione (90 mg, 0.33 mmol) in N,N-dimethylformamide (2 mL) was added EDC (75 mg, 0.39 mmol), HOBT (53 mg, 0.39 mmol) and cyclohexane-propionic acid (61 mg, 0.39 mmol). This was stirred at room temperature for 2 hours. The reaction was diluted with ethyl acetate (50 mL), then washed with 10% aqueous potassium hydrogen sulfate (25 mL) then saturated aqueous sodium hydrogen carbonate (25 mL) and finally, brine (25 mL). The organic layers were combined, dried over anhydrous magnesium sulfate, filtered, and concentrated in vacuo. The residue was chromatographed on silica gel eluting with 25–40% ethyl acetate:hexane to give 92 mg of product (93%), which was crystallized from ethyl acetate/hexane to give colorless crystals (70 mg). mp 152°–153° C.

¹H NMR (300 MHz, CDCl₃) d 7.45–7.38 (m, 2H), 7.35–7.30 (m, 2H), 6.782 (br d, J=7.9 Hz, 1H), 5.06 (J=7.9 Hz, 1H), 4.50 (sep, J=7.0 Hz, 1H), 2.35–2.29 (m, 2H), 1.76–1.60 (m, 5H), 1.60–1.5 (m, 4H), 1.50 (d, J=7 Hz, 6H), 1.30–1.10 (m, 2H), 1.27 (d, J=7 Hz, 6H), 0.95–0.81 (m, 2H).

Anal. Calcd. for: C₂₄H₃₅N₃O₃.0.15 H2O: C: 69.25; H: 8.55; N: 10.09.

Found: C: 69.21; H: 8.40; N: 10.16.

The compounds of Examples 2, 3, 4 and 5 were prepared from 3-amino-1,5-bis-(2-propyl)-1,5-benzodiazepin-2,4-dione by a procedure substantialy as described above for the preparation of Example 1 (Step I-E).

Example 2

N-(2,4-Dioxo-1-5-bis(2-propyl)-2,3,4,5-tetrahydro-1H-1,5-benzodiazepin-3-yl)-3-(2,4-dichlorophenyl) propionamide

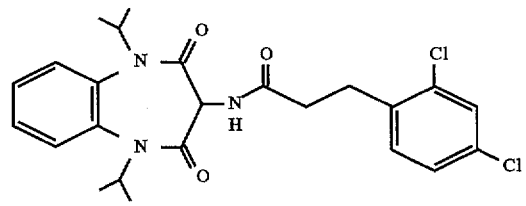

m.p.=168°–169° C.

¹H NMR (300 MHz, CDCl₃) d 7.46–7.11 (m, 7H), 6.74 (d, J=8.0 Hz, 1H), 5.02 (J=8.0 Hz, 1H), 4.51 (sep, J=7.0 Hz, 2H), 3.03 (t, J=7.6 Hz, 2H), 2.65 (t, J=7.6 Hz, 2H), 1.52 (d, J=7.0 Hz, 3H), 1.27 (d, J=7.0 Hz, 3H).

Anal. Calcd. for C₂₄H₂₇N₃O₃Cl₂:
C: 60.51; H: 5.71; N: 8.82.

Found: C: 60.31; H: 5.69; N: 8.86.

Example 3

N-(2,4-Dioxo-1-5-bis(2-propyl)-2,3,4,5-tetrahydro-1H-1,5-benzodiazepin-3-yl)-2-(3,5-dichlorophenyl) acetamide

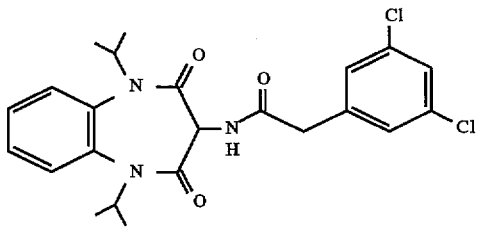

m.p.=151°–152° C.

¹H NMR (300 MHz, CDCl₃) d 7.46–7.09 (m, 7H), 6.76 (d, J=7.9 Hz, 1H), 4.98 (J=7.9 Hz, 1H), 4.51 (sep, J=7.1 Hz, 2H), 3.61 (s, 2H), 1.52 (d, J=7.1 Hz, 3H), 1.27 (d, J=7.1 Hz, 3H).

Anal. Calcd. for C₂₃H₂₅N₃O₃Cl₂:
C: 59.75; H: 5.45; N: 9.09.

Found: C: 59.68; H: 5.45; N: 9.06.

Example 4

N-(2,4-Dioxo-1-5-bis(2-propyl)-2,3,4,5-tetrahydro-1H-1,5-benzodiazepin-3-yl)-2-(2,4-dichlorophenyl) acetamide

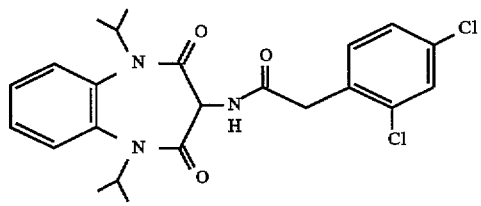

m.p.=185°–186° C.

¹H NMR (300 MHz, CDCl₃) d 7.44–7.18 (m, 7H), 6.85 (d, J=7.5 Hz, 1H), 4.98 (J=7.5 Hz, 1H), 4.51 (sep, J=6.9 Hz, 2H), 3.78 (s, 2H), 1.55 (d, J=6.9 Hz, 3H), 1.24 (d, J=6.9 Hz, 3H).

Anal. Calcd. for: C₂₃H₂₅N₃O₃Cl₂: C: 59.75; H: 5.45; N: 9.09.

Found: C: 59.53; H: 5.41; N: 9.09.

Example 5

N-(2,4-Dioxo-1-5-bis(2-propyl)-2,3,4,5-tetrahydro-1H-1,5-benzodiazepin-3-yl)-3,4-dichlorobenzamide

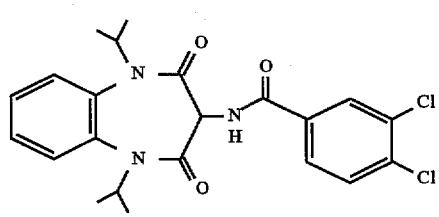

m.p.=118°–125° C.

¹H NMR (300 MHz, CDCl₃) d 8.00–7.23 (m, 8H), 5.15 (J=7.6 Hz, 1H), 4.55 (sep, J=6.9 Hz, 2H), 1.54 (d, J=6.8 Hz, 3H), 1.30 (d, J=6.9 Hz, 3H).

Anal. Calcd. for C₂₂H₂₃N₃O₃C₂: C: 58.94; H: 5.17; N: 9.37.

Found: C: 58.82; H: 5.20; N: 8.94.

Example 6

N-(2,4-Dioxo-1-(2-propyl)-5-(2,2,2-trifluoroethyl)-2,3,4,5-tetrahydro-1H-1,5-benzodiazepin-3-yl)-2-(3,5-dichlorophenyl) acetamide

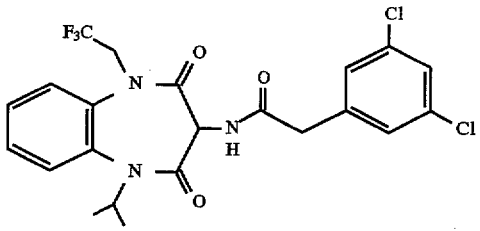

Step II-A: 1-(2-propyl)-1,5-benzodiazepine-2,4-dione

A solution of 1,5-benzodiazepine-2,4-dione (5.5 g, 0.031 mole) in DMSO (70 mL) was treated with cesium carbonate (10.17 g, 0.031 mole) and 2-iodopropane (5.27 g, 0.031 mole). The reaction was heated to 80° C. for two hours and then stirred at room temperature for 18 hours. The mixture was diluted with ethyl acetate (400 mL) and poured into water (500 mL). The organic layer was separated and the aqueous layer was extracted again with ethyl acetate (400 mL). The organic layers were combined, dried over anhydrous magnesium sulfate, filtered and concentrated in vacuo. The residue was chromatographed on silica gel eluting with 3:1 ethyl acetate:hexane to give 560 mg of product.

$^1$H NMR (300 MHz, CDCl$_3$) d 8.6 (s, 1H), 7.40 (app d, J=5 Hz, 1H), 7.25 (m, 2H), 7.18 (app d, J=5 Hz, 1H), 4.60 (sep, J=7 Hz, 1H), 3.3 (s, 2H), 1.50 (d, J=7 Hz, 3H), 1.20 (d, J=7 Hz, 3H).

Step II-B: 1-(2-propyl)-5-(2,2,2-trifluoroethyl)-1,5-benzodiazepine-2,4-dione A solution of 1-(2-propyl)-1,5-benzodiazepine-2,4-dione (0.55 g, 0.0025 mole) in N,N-dimethylformamide (5 mL) at room temperature was treated with cesium carbonate (1.64 g, 0.005 mole) and trifluoroethyl iodide (1.06g, 0.005 mole), and heated to 80° C. for 2 hours. The reaction was cooled to room temperature and poured into a solution of saturated sodium hydrogen carbonate (100 mL) and extracted with ethyl acetate (3×50 mL). The organic layers were combined, dried over anhydrous magnesium sulfate, filtered, and concentrated in vacuo. The residue was chromatographed on silica gel eluting with 1:1 ethyl acetate/hexane to give 440 mg of product.

$^1$H NMR (300 MHz, CDCl$_3$) d 7.50–7.40 (m, 1H), 7.7.35–7.20 (m, 3H), 5.27 (d q, J=6.9,7.1 Hz, 1H), 4.50 (sep, J=7 Hz, 1H), 4.05 (d q (app sextet), J=7.1 Hz, 1H), 3.35 (s, 2H), 1.55 (d, J=6.9 Hz, 3H), 1.28 (d, J=7.1 Hz, 3H).

Step II-C: 3-Azido-1-(2-propyl)-5-(2,2,2-trifluoroethyl)-1,5-benzodiazepine-2,4-dione To a stirring solution of 1-(2-propyl)-5-(2,2,2-trifluoroethyl)-1,5-benzodiazepine-2,4-dione (440 mg, 1.46 mmole) in tetrahydrofuran (12 mL), which was cooled to −78° C. in a dry ice/acetone bath, was added dropwise potassium tert-butoxide (1M in tetrahydrofuran, 1.61 mL, 1.61 mmole). After ten minutes, 2,4,6-triisopropylbenzenesulfonyl azide (495 mg, 1.61 mmole) in tetrahydrofuran (5 mL) was added dropwise. After ten minutes, acetic acid (0.35 mL, 5.84 mmole) in tetrahydrofuran (5 mL) was added in one portion and the reaction was warmed to room temperature over three hours. The reaction was poured into a solution of saturated sodium hydrogen carbonate (200 mL) and extracted with ethyl acetate (3×100 mL). The organic layers were combined, dried over anhydrous magnesium sulfate, filtered, and concentrated in vacuo. The residue was chromatographed on silica gel eluting with 1:3 ethyl acetate:hexane to give 350 mg of product identified as the axial conformer and 35 mg of the equatorial isomer. NMR data is given for the major isomer.

$^1$H NMR (300 MHz, CDCl$_3$) d 7.48–7.25 (m, 4H), 5.21 (dq, J=8, 15 Hz, 1H), 5.04 (s, 1H), 4.45 (sep, J=7 Hz, 1H), 4.13 (dq (app sextet), J=7.5, 15 Hz, 1H), 1.53 (d, J=7.0 Hz, 3H), 1.37 (d, J=7 Hz, 3H).

Step II-D: 3-Amino-1-(2-propyl)-5-(2,2,2-trifluoroethyl)-1,5-benzodiaz.epine-2,4-dione To a stirring suspension of 10% Pd/C (100 mg) in ethanol (10 mL) was added a solution of 3-azido-1-(2-propyl)-5-(2,2,2-trifluoroethyl)-1,5-benzodiazepine-2,4-dione (390 mg, 1.14 mmole) in ethanol (10 mL). The mixture was hydrogenated at 15 psi H$_2$ for 3 hours. The catalyst was filtered off and the ethanol evaporated at reduced pressure to give the product amine (380 mg).

Step II-E: N-(2,4-Dioxo-1-(2-propyl)-5-(2,2,2-trifluoroethyl)-2,3,4,5-tetrahydro-1H-1,5-benzodiazepin-3-yl)-2-(3,5-dichlorophenyl) acetamide To a stirring solution of 3-amino-1-(2-propyl)-5-(2,2,2-trifluoroethyl)-1,5-benzodiazepine-2,4-dione (180 mg, 0.57 mmol) in N,N-dimethylformamide (2 mL) was added EDC (131 mg, 0.69 mmol), HOBT (46 mg, 0.34 mmol) and 3,5-dichlorophenylacetic acid (140 mg, 0.69 mmol). The reaction was stirred at room temperature for 2 hours. The reaction was diluted with ethyl acetate (50 mL), then washed with 10% aqueous potassium hydrogen sulfate (25 mL) then saturated aqueous sodium hydrogen carbonate (25 mL) and finally, brine (25 mL). The organic layers were combined, dried over anhydrous magnesium sulfate, filtered, and concentrated in vacuo. The residue was chromatographed on silica gel eluting with 25–40% ethyl acetate:hexane to give 100 mg of product which was crystallized from ethyl acetate/hexane to give colorless crystals (70 mg). m.p.= 185°–186° C.

$^1$H NMR (300 MHz, CDCl$_3$) d 7.48–7.12 (m, 7H), 6.89 (d, J=7.3 Hz, 1H), 5.34–5.16 (m, 1H), 5.07 (J=7.3 Hz, 1H), 4.46 (sep, J=7.1 Hz, 1H), 4.12–4.00 (m, 1H), 3.60 (s, 2H), 1.56 (d, J=6.9 Hz, 3H), 1.32 (d, J=6.9 Hz, 3H).

Anal. Calcd. for $C_{22}H_{20}N_3O_3Cl_2F_3$: C: 52.60; H: 4.01; N: 8.37.

Found: C: 52.27; H: 3.99; N: 8.18.

Example 7

N-(2,4-Dioxo-1-(2-propyl)-5-(2,2,2-tfifluoroethyl)-2,3,4,5-tetrahydro-1H-1,5 -benzodiazepin-3-yl)-2-(2,4-dichlorophenyl) acetamide

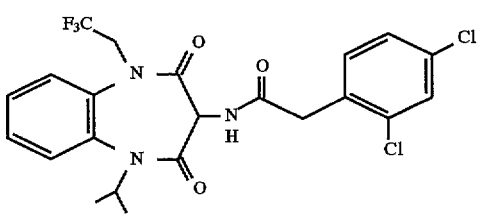

Starting with the appropriate amino acid the compound of this example was preapred using the the method of Example 6. The compound had a melting point of 175°–176° C.

$^1$H NMR (300 MHz, CDCl$_3$) d 7.48–7.17 (m, 7H), 6.89 (d, J=7.3 Hz, $^1$H), 5.32–5.16 (m, 1H), 5.09 (J=7.3 Hz, 1H), 4.45 (sep, J=6.9 Hz, 1H), 4.12–3.97 (m, 1H), 3.77 (s, 2H), 1.51 (d, J=6.8 Hz, 3H), 1.31 (d, J=7.0 Hz, 3H).

Anal. Calcd. for C$_{22}$H$_{20}$N$_3$O$_3$Cl$_2$F$_3$: C: 52.60; H: 4.01; N: 8.37.

Found: C: 52.23; H: 3.99; N: 8.31.

What is claimed is:

1. A compound of the structural formula I

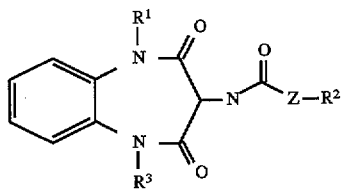

FORMULA I where

R$^1$ and R$^3$ are independently C$_{1-6}$ alkyl, either straight or branched chain; substituted C$_{1-6}$ alkyl, either straight or branched chain wherein the substituents are selected from F, C$_{3-8}$ cycloalkane, —OH, —CF$_3$, and Z is
1) C$_{1-6}$ alkyl, either straight or branched chain,
2) substituted C$_{1-6}$ alkyl, either straight or branched chain, wherein the substituents are selected from F, OH, NO$_2$,
3) C$_{2-4}$ alkenylene, either straight or branched chain,
4) C$_{3-6}$ cycloalkane,
5) C$_{3-6}$ cycloalkylene, or
6) single bond;

R$^2$ is
1) phenyl, either unsubstituted or substituted with one or two substituents selected from
  a) —NO$_2$, —OH,
  b) —Cl, Br, F, or I,
  c) —CF$_3$,
  d) —C$_{1-3}$ alkyl,
  e) —C$_{1-3}$ alkoxy,
  f) —CN,
  g) -methylenedioxy,
2) C$_{5-7}$ cycloalkyl, either unsubstituted or substituted with one or two substituents selected from
  a) —NO$_2$,
  b) —F,
  c) —CF$_3$,
  d) —C$_{1-3}$ alkyl,
  e) —C$_{1-3}$ alkoxy,
  f) —CN,
  g) —methylenedioxy, or pharmaceutically acceptable salts, hydrates and crystal forms thereof.

2. The compound of claim 1 selected from the group consisting of N-(2,4-Dioxo-1,5-bis-(2-propyl)-2,3,4,5-tetrahydro-1H-1,5-benzodiazepin-3-yl)-3-cyclohexyl propionamide

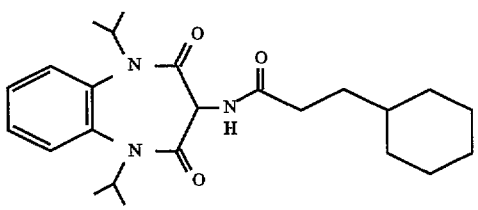

N-(2,4-Dioxo-1-5-bis(2-propyl)-2,3,4,5-tetrahydro-1H-1,5-benzodiazepin-3-yl)-3-(2,4-dichlorophenyl) propionamide,

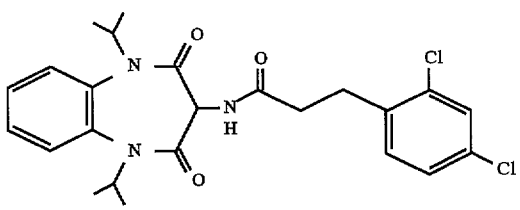

N-(2,4-Dioxo-1-5-bis(2-propyl)-2,3,4,5-tetrahydro-1 H-1,5-benzodiazepin-3-yl)-2-(3,5-dichlorophenyl) acetamide,

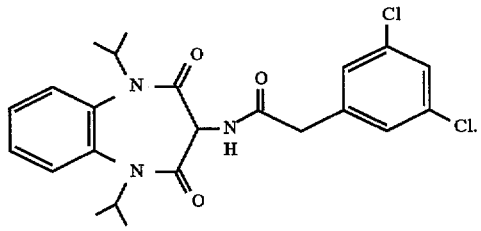

N-(2,4-Dioxo-1-5-bis(2-propyl)-2,3,4,5-tetrahydro-1H-1,5-benzodiazepin-3-yl)-2-(2,4-dichlorophenyl) acetamide,

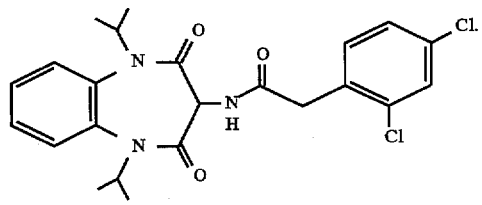

N-(2,4-Dioxo-1-5-bis(2-propyl)-2,3,4,5-tetrahydro-1H-1,5-benzodiazepin-3-yl)-3,4-dichlorobenzamide,

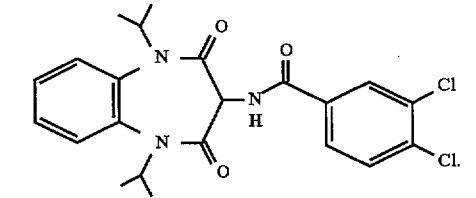

N-(2,4-Dioxo-1-(2-propyl)-5-(2,2,2-trifluoroethyl)-2,3,4,5-tetrahydro-1H-1,5-benzodiazepin-3-yl)-2-(3,5-dichlorophenyl) acetamide,

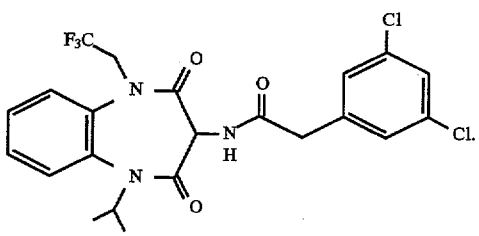

N-(2,4-Dioxo-1-(2-propyl)-5-(2,2,2-trifluoroethyl)-2,3,4,5-tetrahydro-1H-1,5-benzodiazepin-3-yl)-2-(2,4-dichlorophenyl) acetamide,

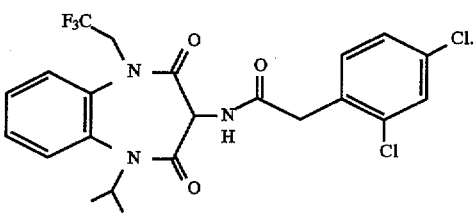

3. The compound of claim 1 which is N-(2,4-Dioxo-1,5-bis-(2-propyl)-2,3,4,5-tetrahydro-1H-1,5-benzodiazepin-3-yl)-3-cyclohexyl propionamide.

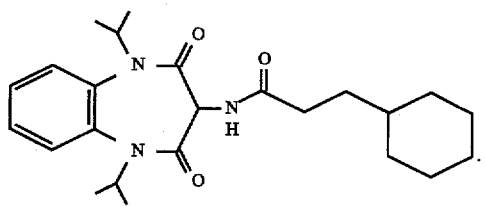

4. The compound of claim 1 which is N-(2,4-Dioxo-1-5-bis(2-propyl)-2,3,4,5-tetrahydro-1H-1,5-benzodiazepin-3-yl)-3-(2,4-dichlorophenyl) propionamide

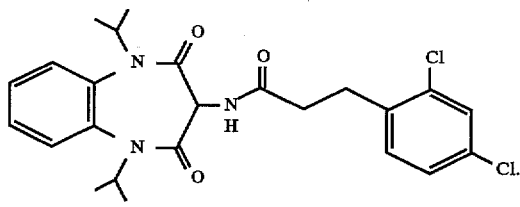

5. The compound of claim 1 which is N-(2,4-Dioxo-1-5-bis(2-propyl)-2,3,4,5-tetrahydro-1H- 1,5-benzodiazepin-3-yl)-2-(3,5-dichlorophenyl) acetamide.

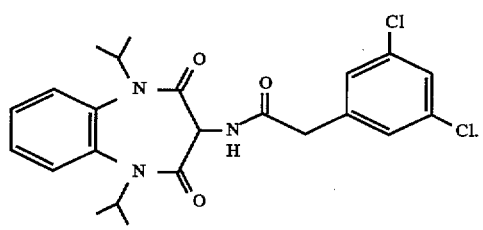

6. The compound of claim 1 which is N-(2,4-Dioxo-1-5-bis(2-propyl)-2,3,4,5-tetrahydro-1H-1,5-benzodiazepin-3-yl)-2-(2,4-dichlorophenyl) acetamide.

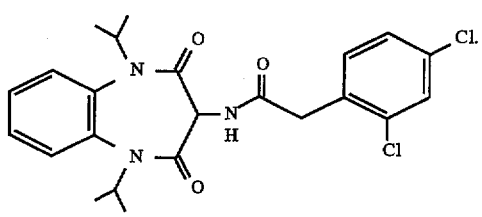

7. The compound of claim 1 which is N-(2,4-Dioxo-1-5-bis(2-propyl)-2,3,4,5-tetrahydro-1H-1,5-benzodiazepin-3-yl)-3,4-dichlorobenzamide.

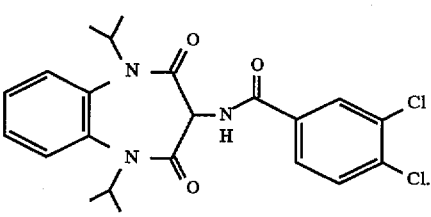

8. The compound of claim 1 which is N-(2,4-Dioxo-1-(2-propyl)-5-(2,2,2-trifluoroethyl)-2,3,4,5-tetrahydro-1H-1,5 -benzodiazepin-3-yl)-2-(3,5-dichlorophenyl) acetamide

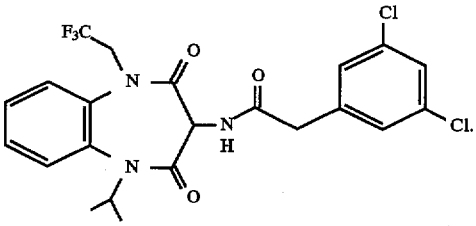

9. The compound of claim 1 which is N-(2,4-Dioxo-1-(2-propyl)-5-(2,2,2-trifluoroethyl)-2,3,4,5-tetrahydro-1H-1,5-benzodiazepin-3-yl)-2-(2,4-dichlorophenyl) acetamide

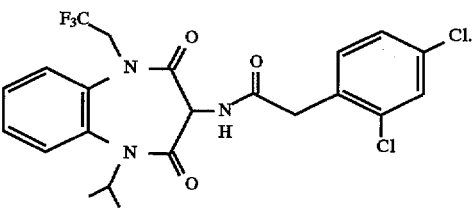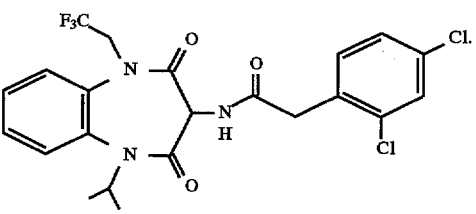

10. A pharmaceutical formulation comprising a pharmaceutically acceptable carrier and a therapeutically effective amount of the compound of claim 1 or a pharmaceutically acceptable salt, crystal form or hydrate thereof.

11. A method of preventing or treating arrhythmia which comprises the administration to a patient in need of such treatment of an antiarrhythmically effective amount of the compound of claim 1.

12. A method of preventing or treating arrhythmia which comprises the administration to a patient in need of such treatment of an antiarrhythmically effective amount of the compound of the structural formula

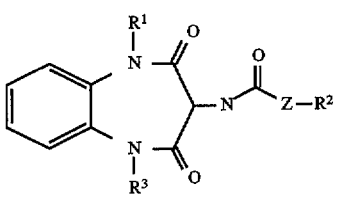

wherein $R^1$ and $R^3$ are independently $C_{1-6}$ alkyl, either straight or branched chain; substituted $C_{1-6}$ alkyl, either straight or branched chain wherein the substituents are selected from F, $C_{3-8}$ cycloalkane, —OH, —$CF_3$, and Z is
1) $C_{1-6}$ alkyl, either straight or branched chain,
2) substituted $C_{1-6}$ alkyl, either straight or branched chain, wherein the substituents are selected from F, OH, NO2,
3) $C_{2-4}$ alkenylene, either straight or branched chain,
4) —$(CH_2)_m$—W—$(CH_2)_n$— wherein m and n are independently 0, 1, 2, 3 or 4 and W is —O—, —S— or —NH,
5) $C_{3-6}$ cycloalkane,
6) $C_{3-6}$ cycloalkylene, or
7) single bond;

$R^2$ is
1) phenyl, either unsubstituted or substituted with one or two substituents selected from
    a) —$NO_2$, —OH,
    b) —Cl, Br, F, or I,
    c) —$CF_3$,
    d) —$C_{1-3}$ alkyl,
    e) —$C_{1-3}$ alkoxy,
    f) —CN,
    g) -methylenedioxy,
$C_{5-7}$ cycloalkyl, either unsubstituted or substituted with one or two substituents selected from
    a) —$NO_2$,
    b) —F,
    c) —$CF_3$,
    d) —$C_{1-3}$ alkyl,
    e) —$C_{1-3}$ alkoxy,
    f) —CN,
    g) -methylenedioxy, or pharmaceutically acceptable salts, hydrates and crystal forms thereof.

* * * * *